United States Patent [19]
Ternansky et al.

[11] Patent Number: 5,990,137
[45] Date of Patent: Nov. 23, 1999

[54] METHOD OF INHIBITING NADPH OXIDASE

[75] Inventors: Robert J. Ternansky, Carlsbad; Karen L. Valentino, San Diego; Donald S. Karanewsky, Escondido, all of Calif.

[73] Assignee: Idun Pharmaceuticals, Inc., La Jolla, Calif.

[21] Appl. No.: 09/092,461

[22] Filed: Jun. 5, 1998

Related U.S. Application Data

[62] Division of application No. 08/676,822, Jul. 8, 1996.
[51] Int. Cl.$^6$ .......................... A61K 31/44; A61K 31/41; A61K 31/15; A61K 31/135
[52] U.S. Cl. .......................... 514/357; 514/361; 514/639; 514/646; 514/647
[58] Field of Search .................................. 514/357, 361, 514/639, 646, 647

[56] References Cited

U.S. PATENT DOCUMENTS

| | | | |
|---|---|---|---|
| 4,015,014 | 3/1977 | Vatne et al. | 424/324 |
| 4,256,108 | 3/1981 | Theeuwes | 128/260 |
| 4,265,874 | 5/1981 | Bonsen et al. | 424/15 |
| 4,564,636 | 1/1986 | Kaplan | 514/567 |

OTHER PUBLICATIONS

Dewhirst, "Structure–Activity Relationships for Inhibition of Prostaglandin Cyclooxygenase by Phenolic Compounds," *Prostaglandins* 20(2): 209–222, 1980.

Gaur et al., *Chemical Abstract* 116: Abstract No. 151378u, 1992.

Hansen et al., "Re–examination and further development of a precise and rapid dye method for measuring cell growth/cell kill," *Journal of Immunological Methods* 119: 203–210, 1989.

Hogquist et al., "Release of IL–1 From Mononuclear Phagocytes," *J. Immunology* 147: 2181–2186, 1991.

Machon and Ryng, "Synthesis and Biological Properties of 5–Benzoylamino–3–Methyl–4–Isoxazolocarboxylic Acid Derivatives," *Arch. Immunol. Ther. Exp.* 29(6): 813–821, 1981.

Mosmann, "Rapid Colorimetric Assay for Cellular Growth and Survival: Application to Proliferation and Cytotoxicity Assays," *Journal of Immunological Methods* 65: 55–63, 1983.

Mrowietz et al., "Inhibition of Human Monocyte Functions by Anthralin," *British Journal of Dermatology* 127: 382–386, 1992.

Ramanathan et al., "Biological Activity of Some 2–Amino 4,5,6,7–Tetrahydro Benzo (b)–Thiophenes and Their Derivatives," *J. Indian Chem. Soc. LV*: 822–825, 1978.

Slater et al., "Studies on Succinate–Tetrazolium Reductase Systems, III. Points of Coupling of Four Different Tetrazolium Salts," *Biochim. Biophys. Acta.* 77: 383–393, 1963.

Sozzani et al., "The Signal Transduction Pathway Involved in the Migration Induced by a Monocyte Chemotactic Cytokine," *The Journal of Immunology* 147: 2215–2221, 1991.

Stolk et al., "Characteristics of the Inhibition of NADPH Oxidase Activation in Neutrophilis by Apocynin, a Methoxy–substituted Catechol," *Am. J. Respir. Cell Mol. Biol.* 11: 95–102, 1994.

Synderman, "Methods for Studying Mononuclear Phagocytes," Adams et al. (eds.), Academic Press, New York, 1981, pp. 535–547.

Wahl et al., "Current Protocols in Immunology," Coligan et al. (eds.), 1991, p. 7.6.1.

Wahl et al., "Isolation of Human Mononuclear Cell Subsets by Counterflow Centrifugal Elutriation (CCE)," *Cellular Immunology* 85: 373–383, 1984.

Zigmond et la., "Leukocyte Locomotion and Chemotaxis," *The Journal of Experimental Medicine* 137: 387–410, 1973.

*Primary Examiner*—Theodore J. Criares
*Attorney, Agent, or Firm*—Seed and Berry LLP

[57] ABSTRACT

The instant methods employs pharmaceutical compositions comprising aromatic azines; and imines, of the Formula 1 to selectively inhibit inflammation by preventing the oxidating burst from phagocytic leukocytes caused by NADPH Oxidase.

33 Claims, No Drawings

METHOD OF INHIBITING NADPH OXIDASE

CROSS-REFERENCE TO RELATED APPLICATION

This application is a divisional of U.S. patent application Ser. No. 08/676,822, filed Jul. 8, 1996, now pending.

BACKGROUND OF THE INVENTION

The present invention relates to methods for treating inflammatory disorders. More specifically, the present invention concerns the control of the generation of free radicals in the immune response.

Phagocytic leukocytes are an important part of the body's defense against invasions of pathogenic microbes and cleansing mechanisms for dead and dying cells. Phagocytic leukocyte is a term that encompasses neutrophils, eosinophils, and macrophages. These phagocytic cells are most often brought to the source of invasion by the bloodstream. Certain macrophages also reside in the tissues of various organs. Once these phagocytic cells are brought in contact with microbes or cellular debris they engulf, or "phagocytize", the material. The destruction of the engulfed material is brought about by the reaction of such material with highly reactive chemical species generated by membrane-bound enzymes in the phagocytic cell. In particular, the enzyme NADPH oxidase catalyzes the consumption of oxygen by producing a superoxide anion ($O_2^-$) according to the following formula:

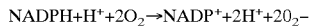

$$NADPH + H^+ + 2O_2 \rightarrow NADP^+ + 2H^+ + 2O_2^-$$

The superoxide anion is able to pass through cell membranes through anion channels to the enveloped biological material. While the superoxide anion may have some direct toxic effects on the engulfed material, it also exerts its toxicity through its conversion to other toxic products known collectively as reactive oxygen species (ROS). Such conversions are happening both chemically and enzymatically within the phagocyte.

Unfortunately, during the process of phagocytosis, these ROS escape from the phagocytic cells into the surrounding cytosol, contacting normal cells in healthy tissue. Such cells and tissues have developed an extensive array of protective enzymic and non-enzymic antioxidants that will decompose these potentially injurious oxidizing agents. During the inflammatory response to these invading microbes, these defenses degrade most oxidants that escape phagocytic cells, thereby limiting the injury to the surrounding tissue until the inflammatory response subsides. However, sustained production of ROS as during chronic inflammation can overwhelm these cellular defenses and damage the healthy tissue. The overproduction of ROS is implicated in the pathogenesis of many diseases, e.g., respiratory distress syndromes, rheumatoid arthritis, ischemia-reperfusion injury and inflammatory bowel disease.

Thus, modulating the production and toxicity of ROS by neutrophils and macrophages would offer one approach to treating inflammatory diseases such as inflammatory bowel disease. In recent: years, three strategies have evolved based on this approach. One such effort has focused on the removal of oxygen radicals with scavenger enzymes such as superoxide dismutase, catalase or similar preparations. Unfortunately, a complicating factor arising in the treatment of chronic inflammatory diseases with these agents is establishing a continuous systemic supply of the scavenger enzymes, as these are rapidly degraded and removed from the body by mechanisms such as digestion by peptidases and the like. Attempts have also been made to identify non-protein mimics of superoxide dismutase but to date such efforts have been unsuccessful.

A second approach had been the prevention of iron-dependent ROS formation by chelation of iron with compounds such as desferrioxamine. A third approach has been to prevent the generation of radicals by NADPH oxidase through the use of compounds such as diphenylene iodonium. Unfortunately, various side effects (including lack of specificity for enzyme inhibitors) complicate the clinical application of the drugs used in these latter two approaches for the treatment of inflammatory diseases.

Thus, it would be advantageous to discover methods which modulate or otherwise ameliorate the oxidative burst pathway of phagocytes and other types of immune cells for use in treatments for inflammatory diseases such as inflammatory bowel disorder.

SUMMARY OF THE INVENTION

In one aspect, this invention is directed to a method for inhibiting the effects of the oxidative burst of phagocytic leukocytes which comprises administering to a host a pharmaceutical composition comprising an effective amount of the compound of the formula:

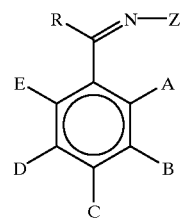

wherein in the above formula:
a) A, B, C, D, E independently can be hydroxy, thiol, $C_1$ to $C_6$ alkyl, $C_1$ to $C_4$ alkoxy, halo, hydrogen atom, $C_1$ to $C_4$ alkylthio, amino, or mono- or di-substituted amino;
b) R is $C_1$ to $C_6$ alkyl, $C_7$ to $C_{12}$ alkylphenyl, $C_7$ to $C_{12}$ substituted alkyphenyl, or a hydrogen atom;
c) Z is a heterocyclic ring, phenyl, or a substituted phenyl;
or wherein Z is
(d) a group of the formula:

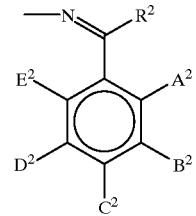

wherein $A^2$, $B^2$, $C^2$, $D^2$, $E^2$ or $R^2$ can be the same or different as A, B, C, D, E or R, respectively, and are as defined as A, B, C, D, E, and R above, respectively.

Another aspect of the invention are pharmaceutical compositions for inhibiting the effects of the oxidative burst of phagocytic leukocyte comprising a compound of the above formula and a pharmaceutically-acceptable carrier.

Yet another aspect of the invention is a method of treating free-radical-generating inflammatory conditions in a mammal administering an effective amount of a pharmaceutical composition comprising a compound of the above formula and a pharmaceutically-acceptable carrier.

DETAILED DESCRIPTION OF THE INVENTION

One aspect of this invention is directed to a method for inhibiting the effects of the oxidative burst of phagocytic leukocytes, which comprises administering to a host a pharmaceutical composition comprising an effective amount of the compound of the Formula I:

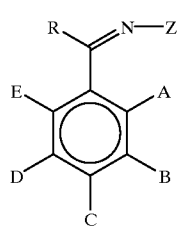

I wherein in the above Formula I:
a) A, B, C, D, E independently can be hydroxy, thiol, $C_1$ to $C_6$ alkyl, $C_1$ to $C_4$ alkoxy, halo, a hydrogen atom, $C_1$ to $C_4$ alkylthio, amino, or mono- or di-substituted amino;
b) R is $C_1$ to $C_6$ alkyl, $C_7$ to $C_{12}$ alkylphenyl, or a hydrogen atom;
c) Z is a heterocyclic ring, phenyl, or a substituted phenyl;
or wherein Z is
(d) a group of the formula:

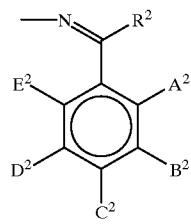

wherein $A^2$, $B^2$, $C_2$, $D^2$, $E^2$ or $R^2$ can be the same or different as A, B, C, D, E or R, respectively, and are as defined above as for A, B, C, D, E, and R, respectively.

The term "$C_1$ to $C_4$ alkoxy" as used herein denotes groups such as methoxy, ethoxy, n-propoxy, isopropoxy, n-butoxy, t-butoxy and the like.

The term "substituted chenyl" specifies a phenyl group substituted with one or two moieties chosen from the group consisting of halogen, hydroxy, protected hydroxy, cyano, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, amino, protected amino, aminomethyl, protected aminomethyl, trifluoromethyl or N-(methylsulfonylamino).

The term "$C_7$ to $C_{12}$ alkylphenyl" denotes a $C_1$ to $C_6$ alkyl group substituted at any position by a phenyl ring. Examples of such a group include phenylmethyl (benzyl), 2-phenylethyl, 3-phenyl-(n-propyl), 4-phenylhexyl, 3-phenyl-(n-amyl), 3-phenyl-(sec-butyl), and the like. A preferred group is the benzyl group.

The term "$C_7$ to $C_{12}$ substituted alkylphenyl" denotes a $C_7$ to $C_{12}$ alkylphenyl group substituted on the $C_1$ to $C_6$ alkyl portion with one to three groups chosen from halogen, hydroxy, protected hydroxy, amino, protected amino, $C_1$ to $C_7$ acyloxy, nitro, carboxy, protected carboxy, carbamoyl, carbamoyloxy, cyarno, N-(methylsulfonylamino) or $C_1$ to $C_4$ allkoxy; and/or the phenyl group may be substituted with 1 to 3 groups chosen from halogen, hydroxy, protected hydroxy, nitro, $C_1$ to $C_6$ alkyl, $C_1$ to $C_4$ alkoxy, carboxy, protected carboxy, carboxymethyl, protected carboxymethyl, hydroxymethyl, protected hydroxymethyl, aminomethyl, protected aminomethyl, or a N-(methylsulfonylamino) group. As before, when either the $C_1$ to $C_6$ alkyl portion or the phenyl portion or both are di-substituted or trisubstituted, the substituents can be the same or different.

Examples of the term "$C_7$ to $C_{12}$ substituted alkylphenyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4-chloro-3-aminobenzyl, 6-(4-methoxphenyl)-3-carboxy(n-hexyl), 5-(4-amino-methyl phenyl)-3-(aminomethyl)(n-pentyl), and the like.

The term "heterocyclic ring" denotes optionally substituted five-membered or six-membered rings that have 1 to 4 heteroatoms, such as oxygen, sulfur and/or nitrogen, in particular nitrogen, either alone or in conjunction with sulfur or oxygen ring atoms. These five-membered or six-membered rings may be fully unsaturated, partially unsaturated or aromatic, with fully unsaturated rings being preferred. Note that, when Z in the above Formula 1 is a heterocyclic ring containing one or more nitrogen atoms, that such a heterocyclic ring is not bound through a nitrogen atom to the remaining ring structure in the Formula.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heterocyclic ring": thienyl, furyl, pyrrolyl, pyrrolidinyl, imidazolyl, pyrazolyl, thiazolyl, isothiazolyl, oxazolyl, tetrahydrofuranyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, piperazyl, thiazinyl, morphilnyl, oxazinyl, triazinyl, thiadiazinyl, oxadiazinyl, dithiazinyl, dioxazinyl, oxathiazinyl, tetrazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, tetrazolo 1,5-[b]pyridazinyl and purinyl, as well as benzo-fused derivatives, for example benzoxazolyl, benzthiazolyl, benzimidazolyl and indolyl.

A preferred group of methods for inhibiting the effects of oxidative burst utilize azines, thus, in the above Formula 1, wherein Z is a group of the formula:

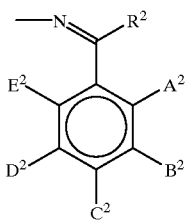

These azines can be symmetrical or unsymmetrical. A preferred group of -methods are wherein the azines used have R and $R^2$ are chosen from the group consisting of a hydrogen atom and methyl; and A, B, C, D, E, $A^2$, $B^2$, $C^2$, $D^2$, $E^2$ are chosen from the group consisting of a hydrogen atom, hydroxy, methoxy, t-butyl, bromo, or ethoxy.

A preferred group of methods utilizing azines are methods wherein the symmetrical azines are administered, that is, wherein in the above Formula 1, $R^2$ and $A^2$, $B^2$, $C^2$, $D^2$, $E^2$ are the same as R, A, B, C, D, and E, respectively.

A preferred group of methods entailing the administration of symmetrical azines are those involving the bis (acetophenone) moieties, wherein R and $R^2$ are methyl. An example of a preferred method occurs when the symmetrical bis(acetophenones) azine bis[4-hydroxy-3-methoxyacetophenone]trans,trans-azine is administered.

Another preferred group of methods wherein symmetrical azines are administered occur when bis(benzaldehydes) compounds are utilized, thus, wherein R and $R^2$ are a hydrogen atom. Preferred methods use bis(benzaldehyde) azines, wherein C and $C^2$ are hydroxy and A, $A^2$, E, and $E^2$ are a hydrogen atom. Examples of such preferred methods within this group occur when bis[4-hydroxy-3-methoxybenzaldehyde]trans,trans-azine, bis[2-bromo-3-hydroxy-4-methoxybenzaldehyde]trans,trans-azine, or bis [4-hydroxybenzaldehyde]trans, trans-azine are administered.

Also encompassed within the methods that administer compounds of Formula 1 are methods employing unsymmetrical azines, wherein in the above Formula 1, at least one of $R^2$, $A^2$, $B^2$, $C^2$, $D^2$, and $E^2$ is different from the corresponding R, A, B, C, D, and E. A preferred class of methods using unsymmetrical azines occur when such azines are unsymmetrical benzaldehyde azines. A preferred group of methods utilizing the unsymmetrical benzaldehyde azines are wherein the compounds utilized have C and $C^2$ chosen from the group consisting of a hydrogen atom and hydroxy; B and $B^2$ are chosen from the group consisting of a hydrogen atom and methoxy; and A, $A^2$, D, $D^2$, E, and $E^2$ are a hydrogen atom. Especially preferred methods are those utilizing [4-hydroxy-3-methoxybenzaldehyde]-[4-hydroxybenzaldehyde] trans,trans-azine and [4-hydroxy-3-methoxybenzaldehyde][benzaldehyde]trans, trans-azine.

Another preferred group of methods utilizing unsymmetrical azines are those utilizing the unsymmetrical acetophenone azines, thus, wherein R and $R^2$ are methyl.

Another class of preferred methods for inhibiting the oxidative burst are those employing imines wherein in the above Formula 1, Z is a heterocyclic ring, phenyl, or substituted phenyl;

A preferred group of methods; employing imines are those wherein the compounds of Formula 1 have A, B, C, D, and E chosen from the group consisting of a hydrogen atom, hydroxy, methoxy, and tert-butyl; and R is a hydrogen atom or methyl. Of the preferred methods utilizing the previous group of preferred imines are those utilizing such compounds formed from a benzaldehyde, wherein R is a hydrogen atom.

A preferred group of methods utilizing imines formed from benzaldehyde are the N-phenyl and N-(substituted) phenylimines, thus, wherein in the above Formula 1, Z is phenyl or substituted phenyl. The third group of methods utilizing these preferred imines are those wherein the substituents on the phenyl group are methoxy or bromo, and especially so when C is a hydroxy group. Examples of such preferred methods are those utilizing N-(3,5-dimethoxy-4-hydroxybenzylidene)-p-methoxyaniline, N-(3-methoxy-4-hydroxybenzylidene)-p-methoxyaniline, N-(3,5-dimethoxy-4-hydroxybenzylidene)-p-bromoaniline, and N-(3,5-dimethoxy-4-hydroxybenzylidene) aniline.

Another aspect of the invention is a pharmaceutical composition for inhibiting the effects of the oxidative burst of phagocytic leukocytes which comprises a compound of Formula I and a pharmaceutically acceptable carrier.

A preferred group of pharmaceutical compositions for inhibiting the effects of oxidative burst utilize azines, thus, in the above Formula 1, wherein Z is a group of the formula:

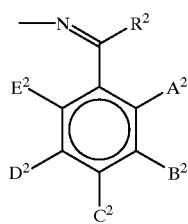

These azines can be symmetrical or unsymmetrical. A preferred group of methods are wherein the azines used have R and $R^2$ are chosen from the group consisting of a hydrogen atom and methyl; and A, B, C, D, E, $A^2$, $B^2$, $C^2$, $D^2$, $E^2$ are chosen from the group consisting of a hydrogen atom, hydroxy, methoxy, t-butyl, bromo, or ethoxy.

A preferred group of pharmaceutical compositions utilizing symmetrical azines are compositions, wherein in the above Formula 1, $R^2$ and $A^2$, $B^2$, $C^2$, $D^2$, $E^2$ are the same as R, A, B, C, D, and E, respectively.

Another preferred group of pharmaceutical compositions wherein utilizing symmetrical occur when bis (benzaldehydes) compounds are utilized, thus, wherein R and $R^2$ are a hydrogen atom. Preferred compositions use bis(benzaldehyde) azines, wherein C and $C^2$ are hydroxy and A, $A^2$, E, and $E^2$ are a hydrogen atom. An example of such preferred methods within this group occur when bis [4-hydroxy-3-methoxybenzaldehyde]trans,trans-azine, a compound of Formula I, is admixed with a pharmaceutical carrier.

Also encompassed within the pharmaceutical composition are compositions employing unsymmetrical azines, wherein in the above Formula I, at least one of $R^2$, $A^2$, $B^2$, $C^2$, $D^2$, and $E^2$ is different from the corresponding R, A, B, C, D, and E. A preferred class of methods using unsymmetrical azines occur when such azines are unsymmetrical benzaldehyde azines. A preferred group of compositions utilizing the unsymmetrical benzaldehyde azines are wherein the compounds utilized have C and $C^2$ chosen from the group consisting of a hydrogen atom and hydroxy; B and $B^2$ are chosen from the group consisting of a hydrogen atom and methoxy; and A, $A^2$, D, $D^2$, E, and $E^2$ are a hydrogen atom. Especially preferred compositions are those utilizing [4-hydroxy-3-methoxybenzaldehyde]-[4-hydroxybenzaldehyde]trans,trans-azine and [4-hydroxy-3-methoxybenzaldehyde][benzaldehyde]trans, trans-azine.

Another class of preferred pharmaceutical compositions are those employing imines wherein in the above Formula 1, Z is a heterocyclic ring, phenyl, or substituted phenyl;

A preferred group of pharmaceutical compositions employing imines are those wherein the compounds of Formula 1 have A, B, C, D, and E chosen from the group consisting of a hydrogen atom, hydroxy, methoxy, and tert-butyl; and R is a hydrogen atom or methyl. Of the preferred compositions utilizing the previous group of preferred imines are those utilizing such compounds formed from a benzaldehyde, wherein R is a hydrogen atom.

A preferred group of compositions utilizing imines formed from benzaldehyde are the N-phenyl and N-(substituted) phenylimines, thus, wherein in the above Formula I, Z is phenyl or substituted phenyl. The third group of compositions utilizing these preferred imines are those wherein the substituents on the phenyl group are methoxy or bromo, and especially so when C is a hydroxy group. Examples of such preferred compositions are those utilizing N-(3,5-dimethoxy-4-hydroxybenzylidene)-p-methoxyaniline, N-(3-methoxy-4-hydroxybenzylidene)-p-methoxyaniline, N-(3,5-dimethoxy-4-hydroxybenzylidene)-p-bromoaniline, and N-(3,5-dimethoxy-4-hydroxybenzylidene)aniline.

Yet another aspect of this invention is a method of treating free-radical-generating inflammatory conditions in a mammal, comprising administering the pharmaceutical composition comprising the compound of Formula I and a pharmaceutically acceptable carrier. Preferred method occurs when the conditions being treated is selected from the group consisting of inflammatory bowel disease, rheumatoid arthritis, granulomatous disease, reperfusion injury from heart attack or stroke, and asthma. More preferred methods occur when the condition is either rheumatoid arthritis, reperfusion injury from heart attack or stroke, inflammatory bowel disease or asthma. Futhermore, preferred of the above methods occurs when pharmaceutical composition comprises one of the compounds set forth below in the Examples or one of the compounds discussed in Table 1 and especially so when the compound is bis[4-hydroxy-3-methoxybenzaldehyde]-trans,trans-azine.

The compounds of Formula 1 can be synthesized according to the following Scheme I:

SCHEME I

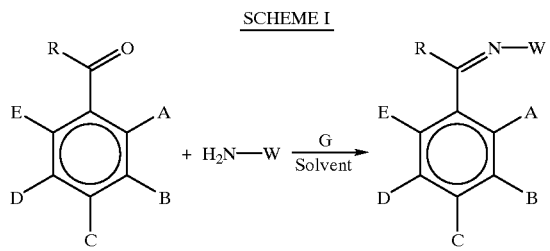

The condensation reaction depicted above in Scheme I is carried out in conditions that are well known in the art. Thus, polar solvents, whether they be protic or aprotic, can be used. Methanol and ethanol are preferred solvents. The reaction can be carried out at room temperature, although temperatures up to and including the reflux temperature of the solvent are also useful. In addition, the reaction mixture can be azeotroped, distilled, treated with titanium tetrachloride or molecular sieves to remove water that is formed in order to shift the equilibrium toward the product. The typical reaction time for that of Scheme I is twenty-four (24) hours. The product can be isolated in the usual manner, most often by flash chromatography over silica.

In particular, the imines used in the instant methods can be formed by first dissolving the aromatic carbonyl substrate in the appropriate solvent and adding the amine reagent ($H_2N$-W) under a nitrogen atmosphere in a 1 to 1 molar ratio. In forming these imines, the amino reagent has W as $C_1$ to $C_6$ alkyl, $C_1$ to $C_4$ alkoxy, $C_7$ to $C_{12}$ alkylphenyl, $C_7$ to $C_{12}$ substituted alkylphenyl, heterocyclic ring, phenyl, and substituted phenyl.

The azines of the above Formula 1 can be formed according to Scheme I above in one of two general fashions. For the symmetrical azines, the amino reagent is hydrazine, in other words, W is an amino group. At least two equivalents of the aromatic carbonyl substrate are dissolved in the solvent and then hydrazine is added and the reaction is stirred under a nitrogen atmosphere according to the general conditions set forth above. For the unsymmetrical azines, the first aromatic carbonyl substrate is combined in at least as 10-fold excess with N,N-(dimethyl)hydrazine and the resulting hydrazone is isolated, reacted with anhydrous hydrazine and the resultant hydrazone is isolated. The isolated hydrazone is reacted with at least one molar equivalent of the second aromatic carbonyl to form the unsymmetrical azine.

The instant methods for inhibiting the oxidative burst of phagocytic leukocytes entail administering pharmaceutical compositions comprising an effective amount of the compounds of Formula 1 orally, topically, parenterally, by inhalation spray or rectally in dosage unit formulations containing conventional non-toxic pharmaceutically acceptable carriers, adjuvants, exipients and vehicles, hereafter collectively referred to as a "pharmaceutically acceptable carrier".

The term parenteral as used herein includes subcutaneous injections, intravenous, intramuscular, intracisternal injection or infusion techniques. In addition to the treatment of warm-blooded hosts such as mice, rats, horses, cattle, sheen, dogs, cats, etc., the compounds of the invention are effective in the treatment of humans.

The pharmaceutical compositions containing the one or more compounds of Formula 1 may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. They may also be coated by the techniques described in the U.S. Pat. Nos. 4,256,108 and 4,265,874 to form osmotic therapeutic tablets for control release.

Pharmaceutical compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Pharmaceutical compositions in the form of aqueous suspensions contain the active materials in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylpyrrolidone, gum tragacanth and gum acacia; dispersing or wetting agents, which may be a naturally-occurring phosphatide, for example lecithin, or condensation products of an alkylene oxide with fatty acids, for example polyoxyethylene stearate, or condensation products of ethyylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Pharmaceutical compositions in the form of oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Pharmaceutical compositions that are dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions for use in the above methods of the invention may also be in the form of oil-in-water emulsions. The oily phase may be a vegetable oil, for example olive oil or arachia oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids an hexicol-anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs are also suitable pharmaceutical formulations for use is the instant methods. Such syrups and elixirs may be formulated with sweetening agents, for example glycerol, propylene glycol, sorbitol or sucrose. Such compositions may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-buzane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The instant methods administering the pharmaceutical compositions comprising the compounds of Formula 1 may also administer said compounds in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, pharmaceutical compositions comprising creams, ointments, jellies, solutions or suspension, etc., containing the compounds of Formula 1 are employed in the instant methods. (For purposes of this application, topical application shall include mouth washes and gargles.) Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservations, absorption promoters to enhance bioavailability, fluorocarbons, and/or other solubilizing or dispersing agents known in the art.

By the term "effective amount", dosage levels of the order of from about 0.05 mg to about 140 mg per kilogram of body weight per day are of the compounds of Formula 1 intended for use. For example, inflammation may be effectively treated by the administration of pharmaceutical compositions from about 0.01 to 50 mg of the compound per kilogram of body weight per day.

The amount of active ingredient that may be combined with the carrier materials to produce a single dosage form will vary depending upon the host treated and the particular mode of administrating. For example, a formulation intended for the oral administration of humans may contain from 0.5 mg to 5 gm of active agent compounded with an appropriate and convenient amount of pharmaceutical carrier which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the inventions encompassing of Formula I and as such, are not intended to limit the invention as set forth in the claims appended thereto.

EXPERIMENTALS

PREPARATION I

MEASUREMENT OF CHEMILUMINESCENCE OF ISOLATED NEUTROPHILS

Part I: Obtain Whole Blood

Whole blood (150 ml) was anticoagulated with Acid Citrate Dextrose (ACD) using a ratio of 1:5 ACD to blood.

Part II: Neutrophil Isolation

All steps are to be performed using polypropylene plastic ware.

1. Dextran Sedimentation
   a. Whole blood (60 ml) was added to each of three 100 ml polypropylene graduated cylinders containing 30 ml of 60% Dextran/Saline. The cylinders were covered securely with Parafilm. The blood was allowed to sediment for approximately 1 hour at room temperature.
   b. The turbid straw-colored layer was harvested from the top of the cylinders into 50 ml conical polypropylene tubes. The white blood cells were pelleted by centrifugation at 240×g (Sorvall at 1200 rpm) for 12 min. at 4° C. with the brake on low.
   c. The supernatant was removed by aspiration and the pooled pellet resuspended in 4–50 ml cold PBS (w/o Ca, Mg). It was then centrifuged at 240×g (Sorvall at 1200 rpm) for 6 min. at 4° C. with the brake on high.
2. Lysis of Contaminating Red Blood Cells.
   a. The supernatant was aspirated and the pellet resuspended in 12 ml of cold cell culture-grade water. The pellet was titrated gently with a pipet for exactly 30 seconds then 4 ml of cold 0.6 M KCl was added. It was then QSed to 50 ml with cold PBS (w/o Ca, Mg) and centrifuged at 300×g (Sorvall TY 6000D at 1400 rpm) for 6 min. at 4° C. with the brake on high.
   b. Step 2.a. was repeated once more.
3. Ficoll-Hypaque Density Gradient Centrifugation
   a. The supernatant was aspirated and the cells were resuspended in 2.5 ml cold PBS (w/o Ca, Mg). The cell suspension was carefully layered over 3 ml Ficoll-Hypaque in a 15 ml polypropylene conical tube. It was then centrifuged at 400×g (Sorvall at 1900 rpm) for 30 min. at 4° C. with the brake on low.
   b. Aspiration occurred down to the neutrophil pellet. The pellet was resuspended fin cold PBS (w/o Ca, Mg) and transferred to a 50 ml conical tube. It was then QSed to 50 ml with cold PBS (w/o Ca, Mg) and centrifuged at 300×g (Sorvall at 1400 rpm) for 6 min. at 4° C. with the brake on high.
   d. The supernatant was aspirated and the pellet resuspended in 50 ml cold PBS (w/o Ca, Mg) and centrifuged at 300×g (Sorvall at 1400 rpm) for 6 min. with the brake on high.
   e. The supernatant was aspirated and the neutrophil pellet resuspended in 4.0 ml cold PBS (w/o Ca, Mg). It was kept on ice. Trypan blue (10 µl) was diluted (1:40) and the cells were counted using a hemacytometer. The cell number and viability by Trypan time exclusion were determined and the results recorded. The cells were diluted to $5.0 \times 10^6$ cells/ml with cold PBS-G (with Ca, Mg) prior to plating for the assay.

Part III: Dose Responses of Compounds of Formula 1

1. The compounds were diluted (five fold dilutions) in deep 96 well plates such that the concentration was ten fold higher than final concentration (50 µM was the highest final concentration).
2. Opsonized zymosan was prepared by suspending 125 mg zymosan particles in 25 ml pooled human serum (5 mg/ml) and incubating them for 20 minutes at 37° C. The suspension was centrifuged and the particles resuspended in 7 ml of PBS-G (with Ca, Mg)(18 mg/ml). It was stored on ice until used (briefly vortexed prior to pipetting).
3. Lucigenin (50 ml of a 250 µM solution)(MW 510.5) was prepared by dissolving 6.4 mg of the solid in 50 ml of PBS-G (with Ca, Mg).
4. PBS-G (10 µl) (with Ca, Mg) was added to the wells in a white 96 well plate.
5. Lucigenin (50 µl of the 250 µM) solution was added to a white 96 well plate.
6. The compound dilutions (10 µl) were added to the appropriate wells.
7. The cell prep was diluted to $5.0 \times 10^6$ cells/ml with PBS-G (with Ca, Mg) in a separate multipipette trough.
8. The neutrophil suspension (20 µl) was added to the appropriate wells.
9. The plate was incubated at 37° C. for three minutes.
10. Zymosan (10 µl of 18 mg/ml) was added to the appropriate wells.
11. The plate was read on the luminometer (Labsystems Luminoskan, Needham Heights, Mass.) for 14 min. at 37° C. on the kinetic mode and the results recorded using the software DeltaSoft.
12. The plate data was exported into Excel to determine percent of control and derive the means and standard deviations for the data. The IC50 was determined graphically from the data and plotted using SigmaPlot. For cases where one concentration (50 µM) was tested, percent inhibition was compared to that seen with 50 µM apocynin.
13. The results are set forth below in Table 1 as "Neutrophil Burst IC50 (Lucigenin)". The results for 50 µM inhibition in the single assay are reported as "Neutrophil Burst Screen Value (% @ 50 µM)".

TABLE 1

| Compound Example Number | Neutrophil Burst IC50 (Lucigenin) (µM) | Neutrophil Burst Screen Value (% @ 50 µM) | Xanthine Oxidase Inhibition IC50 (Integral) (µM) | Cytotox (MTT/Jurkat) |
|---|---|---|---|---|
| 1 | 38 | Not Tested | Not Determinable | 0 |
| 1 | Not Determinable | Not Tested | Not Determinable | 0 |
| 2 | No Effect | Not Tested | No Effect | Not Tested |
| 3 | No Effect | Not Tested | No Effect | Not Tested |
| 4 | No Effect | Not Tested | No Effect | Not Tested |
| 5 | No Effect | Not Tested | No Effect | Not Tested |
| 6 | 13.5 | Not Tested | No Effect | 0 |
| 7 | 33.1 | No Tested | No Effect | 1 |
| 8 | No Effect | Not Tested | No Effect | Not Tested |
| 8 | Not Determinable | — | No Effect | — |
| 9 | 8.7 | Not Tested | 20 | Not |

TABLE 1-continued

| Compound Example Number | Neutrophil Burst IC50 (Lucigenin) ($\mu$M) | Neutrophil Burst Screen Value (% @ 50 $\mu$M) | Xanthine Oxidase Inhibition IC50 (Integral) ($\mu$M) | Cytotox (MTT/Jurkat) |
|---|---|---|---|---|
| 10 | 8.5 | Not Tested | No Effect | Tested 0 |
| 11 | Not Determinable | Not Tested | No Effect | Not Tested |
| 12 | 7.3 | Not Tested | 1.1 | 1 |
| 13 | 44 | Not Tested | No Effect | 0 |
| 14 | No Effect | - - | No Effect | Not Tested |
| 15 | No Effect | — | No Effect | Not Tested |
| 16 | Not Determinable | — | No Effect | 0 |
| 17 | 3.1 | Not Tested | No Effect | 0 |
| 18 | 5 | Not Tested | 32 | 0 |
| 19 | 13.2 | Not Tested | 28 | Not Tested |
| 20 | 9.9 | Not Tested | 34 | Not Tested |
| 21 | 8 | Not Tested | 2.1 | Not Tested |
| 22 | 15.5 | Not Tested | 16.3 | Not Tested |
| 23 | 5 | Not Tested | 14 | Not Tested |
| A | No Effect | 1.10 | No Effect | 0 |
| B | Not Tested | 49.36 | Not Tested | Not Tested |
| C | 4.9 | 85.59 | No Effect | 0 |
| D | Not Determinable | Not Tested | 70 | 1 |
| E | No Effect | Not Tested | No Effect | Not Tested |

A = Bis[3-methoxy-2-hydroxybenzaldehyde]trans,trans-azine (purchased from Maybridge Chemical Co., Ltd., Cornwall, U.K.)
B = 2-N'-(3-methoxy-4-hydroxybenzylidene)-2-amino-1,3-thiazole (purchased from Maybridge Chemical Co, Ltd., Cornwall, U.K.)
C = Bis[4-hydroxy-3-methoxybenzaldehyde]-trans,trans-azine (purchased from Maybridge Chemical Co., Ltd., Cornwall, U.K.)
D = Bis[4-hydroxy-3,5-dimethoxybenzaldehyde]-trans,trans-azine (purchased from Aldrich Chemical Co., Madison, Wisconsin).
E = Bis[Benzaldehyde]trans,trans-azine (purchased from Aldrich Chemical Co., Madison, Wisconsin).

A=Bis[3-methoxy-2-hydroxybenzaldehyde]trans,trans-azine (purchased from Maybridge Chemical Co., Ltd., Cornwall, U.K.)

B=2-N'-(3-methoxy-4-hydroxybenzylidene)-2-amino-1,3-thiazole (purchased from Maybridge Chemical Co, Ltd., Cornwall, U.K.)

C=Bis[4-hydroxy-3-methoxybenzaldehyde]-trans,trans-azine (purchased from Maybridge Chemical Co., Ltd., Cornwall, U.K.)

D=Bis[4-hydroxy-3,5-dimethoxybenzaldehyde]-trans,trans-azine (purchased from Aldrich Chemical Co., Madison, Wis.)

E=Bis[Benzaldehyde]trans,trans-azine (purchased from Aldrich Chemical Co., Madison, Wis.).

PREPARATION II

Specificity Studies for Bis[4-hydroxy-3-methoxybenzaldehyde]trans,trans-azine

To assess specificity of action, the title compound (hereinafter "Azine") was tested for its ability to inhibit other functions of stimulated neutrophils and monocytes. The procedure followed was set forth in Mrowietz et al., *British Journal of Dermatology*, 127:382–386 (1992); Snyderman, Ralph, *Methods for Studying Mononuclear Phagocytes*, ed. Adams, Edelson, and Koren, New York, Academic Press, pp. 535–547 (1981); Sozzani et al., *The Journal of Immunology*, Oct. 1, 1991, pp. 2215–2221; Zigmond et al., *The Journal of Experimental Medicine*, 137:387 (1973); Wahl et al., *Cell Immunol.*, 85:373 (1984); Wahl et al., *Current Protocols in Immunology*, ed. Coligan, Kruisbeek, Margulies, Shevach, and Strober, p. 7.6.1 (1991); Hogquist et al., *J. Immunol*, 147:2181 (1991). The Azine (50 $\mu$M) had no effect on chemotaxis of neutrophils activated by the chemotactic peptide f-Met-Leu-Phe. The Azine (50 $\mu$M) also did not inhibit the secretion of IL-1 or TNF by LPS stimulated or unstimulated monocytes.

PREPARATION III

XANTHINE OXIDASE ASSAY

To evaluate scavenging effects of the compounds of Formula I on superoxide ion ("SO"), SO was generated by a mixture of hypoxanthine and xanthine oxidase and specifically assayed with Lucigenin. This assay was performed in J. Stolk et al., *Am.J. Respir. Cell Mol. Biol.*, 11:95–102 (1994).

Compounds to be tested were made into DMSC 25 mM stock solutions then diluted 1/50, thus 20 $\mu$l of stock solution was added to 980 $\mu$l of PBS tc give a 500 $\mu$M working concentration ×4 of final, then ⅓ serial dilutions were made. The final concentration of top dilution was 125 $\mu$M. The final concentration of most dilutions was 0.057 $\mu$M. The concentration of Lucigenin (bis-N-methylacridenium nitrate) in PBS was formulated to 2.5 mM (i.e., 25.8 mg (51.6) of compound in 20.2194 mls (40.5) PBS).

The DMSO control solution was formulated by adding 20 $\mu$l of DMSC to 980 $\mu$l PBS as for compounds to be tested.

The Allopurinol stock solution was made by dissolving the compound (4.2 mg) in DMSO (1.235 ml)to give a 25 mM stock solution, then diluted as per other compounds.

The hypoxanthine (Substrate) stock solution of 1.5 mM compound in aqueous 0.1M $Na_2CO_3$ solution was formulated by dissolving 58 mg of compound in 28.4 mls of aqueous 0.1M $Na_2CO_3$ solution, then this substrate stock solution (20 mls) was diluted with PBS (30ml).

The stock solution of Xanthine oxidase, Grade I, (buttermilk, x-1875 Sigma, St. Louis, Mo.), was 25 $\mu$/ml in the enzyme then this stock solution was (15 $\mu$l) was diluted into PBS (36 ml).

TABLE 2

| | [Stock] | [Working] | Vol. | [Final] |
|---|---|---|---|---|
| Xanthine Oxidase | 25$\mu$/ml | 10.42m$\mu$/ml | 60$\mu$1 | 3.125m$\mu$/ml |
| Lucigenin | 2.5mM | 2.5mM | 40$\mu$l | 500$\mu$M |
| Compound | 25mM | 500$\mu$M | 50$\mu$l | 125$\mu$M |
| Incubate 10 min in dark, then add: | | | | |
| Hypoxanthine | 1.5mM | 0.6mM | 50$\mu$l | 150 $\mu$M |
| Total Volume | | | 200$\mu$l | |

The reaction was monitored on Labsystem LuminoSkan (Needham Heights, Mass.), and the results were read for at least 15 minutes at 37° C.

Allopurinol is the only strong inhibitor $K_{50}$~1.2 $\mu$M

The results from this experiment are set forth in Table 1 above in the column labeled "Xanthine Oxidase Inhibition IC50".

PREPARATION IV

CYTOTOXICITY ASSAY EMPLOYING JURKAT CELLS

This Assay was performed as set forth in Hansen et al., *Journal of Immunological Methods*, 119:203–210 (19930; Mosmann, *Journal of Immunological Methods*, 65:55– 63 (1983); and Slater et al., *Biochem. Ciophys. Acta,* 77:383 (1963); except as noted below.

Reagents:
Compounds from the following Examples were tested for cytotoxicity using MTT (i.e., 3-[4,5-Dimethylthiazol-2-yl]-2,5-diphenyltetrazolium bromide; Thiazolyl Blue (Sigma, St. Louis, Mo.)).

Reagent Preparation:
MTT Solution
MTT was dissolved in basal culture media at a concentration of 5 mg/ml. If necessary, it was briefly warmed at 37° C. to fully dissolve, passed through a sterile filter, and aliquoted and stored at −20° C. until use.

The Extraction Buffer used was a solution composed of 20% SDS, 2.5% Acetic Acid (80% 6 stock solution), 2.5% 1N Hcl, 50% Dimethylformamide/50% dissolved in distilled water, SDS was dissolved into buffer components with gentle heating and stirring and the resultant solution was filtered and stored until use.

Procedure:
The MTT solution was added in an amount equal to 10% of the culture volume to each well in a 96-well plate containing 100,000 Jurkat cells/well.

The wells were then incubated for 0.5 to 2 hours in standard culture conditions. A volume of extraction buffer equal to the culture volume was added. The 96-well plate was then sealed. The formazan crystals were allowed to extract at 37° C. for four hours. The plate was read on a spectrophotometer [Spectramax 250, Molecular Devices, Sunnyvale, Calif.] at an absorbance wavelength of 560 nm. (The background absorbance measured at 650 nm was subtracted from the value measured at 560 nm.)

The Jurkat cells (Jurkat clone E6-1) were grown using standard conditions supplied by ATCC (American Type Culture Collection—Rockville, Md.).

The compounds diluted in medium (RPMI 1640 plus 10% fetal bovine serum) stock solution of 100 $\mu$M, then this stock solution was further diluted 3-fold before testing in the instant assay.

2-Hydroxy-3-methoxy-E-nitrostyrene tested at 100 $\mu$M as death control cells, incubated under the above conditions at 37° C. overnight.

The Extraction Buffer (100 $\mu$l) was added to each well and the resultant suspension was incubated 4 hours at 37° C.

The results from this procedure are set forth above in Table 1 in the column marked "Cytotox (MTT/Jurkat)". Toxicity was rated "1" if dead cells and >50% reduction in MTT absorbance were observed at 100 $\mu$M of the test compound. Toxicity was rated "2" if dead cells >50% reduction in MTT absorbance were observed at 10 $\mu$M of the test compound. Toxicity was rated "3" if dead cells and >50% reduction in MTT absorbance at 1 $\mu$M test compound.

EXAMPLE 1

Bis[3-Bromo-4-Hydroxy-5-Methoxybenzaldehyde] trans,trans-Azine

3-Bromo-4-hydroxy-5-methoxybenzaldehyde (1 g, 4.33 mmol) was dissolved in methanol (30 ml) with heating. Heat was removed once the solid went into solution. To this solution was added hydrazine hydrate (100.12 mg, 2 mmol, neat liquid) was added by syringe. The reaction was stirred at room temperature under nitrogen for twenty (20) hours. The reaction was then cooled in an ice bath and the resultant precipitate was isolated by filtration. The collected precipitate was washed first with cold methanol then with ether to remove excess hydrazines and was allowed to dry to give 520 mg of a light yellow powder. A portion (10 mgs) of the powder was analyzed by N.M.R. which showed a mixture of the title product and hydrazine. The remaining yellow powder (510 mg, 1.51 mmol) was added to a methanol solution (30 ml) of 2-bromo-3-hydroxy-4-methoxybenzaldehyde (349 mg, 1.51 mmol). The resultant solution was refluxed for two hours and fifteen minutes, then cooled in an ice bath. The precipitate was isolated and washed as above to yield 530 mg of light yellow powder of the title compound: $^1$H NMR (300 MHZ, DMSO-d$_6$); $\delta$ 8.56 (S, 2H), 7.56 (S, 2H), 7.45 (S, 2H), 3.87 (S, 6H).

EXAMPLE 2

Bis[2,3-Dimethoxybenzaldehyde]trans,trans-Azine 2,3-Dimethoxybenzaldehyde (1 g, 6.02 mmol) was dissolved in methanol (30 ml). Hydrazine hydrate (0.145 ml, 150 mg, 3 mmol, neat liquid) was added immediately to the solution by pipet. The reaction was stirred overnight at room temperature under nitrogen to yield a yellow precipitate. The precipitate was isolated by filtration and rinsed with cold methanol and ether to yield the title product: $^1$H NMR (300 MHz, DMSO-d$_6$); $\delta$ 8.84 (S, 2H), 7.57 (d, J=6 Hz, 2H), 7.22–7.12 (m, 4H), 3.82 (d, J=6 Hz, 12H).

EXAMPLE 3

Bis[2-Hydroxy-4-Methoxybenzaldehyde]trans,trans-Azine

2-Hydroxy-4-methoxybenzaldehyde (0.964 g, 6.34 mmol) was dissolved in methanol (30 ml) and to this solution was added hydrazine hydrate (0.158 g, 3.16 mmol, neat liquid) by pipet. The resultant reaction solution was stirred overnight at room temperature and the precipitate was isolated by filtration. The isolated precipitate was washed with cold methanol and ether to yield the title product. $^1$H NMR (300 MHz, DMSO-d$_6$); $\delta$ 8.85 (S, 2H), 7.52 (d, J=9 Hz, 2H), 6.57–6.50 (m, 4H) 3.78 (S, 6H).

EXAMPLE 4

Bis[3-Hydroxy-4-Methoxybenzaldehyde]trans,trans-Azine

3-Hydroxy-4-methoxybenzaldehyde (1 g, 6.57 mmol) was dissolved in methanol (30 ml). To this solution was added hydrazine hydrate (0.161 g, 0.156 ml, 3.21 mmol, neat liquid) by pipet. The reaction was allowed to stir at room temperature overnight. Additional hydrazine hydrate (20 ml) was added and the reaction was allowed to stir for forty-eight (48) hours at room temperature. The resultant precipitate was isolated by filtration then washed with cold methanol to give the title product. $^1$H NMR (300 MHz, DMSO-d$_6$); $\delta$ 9.22 (S, 2H), 8.49 (S, 2H), 7.33 (S, 2H), 7.20 (d, J=6 Hz, 2H), 7.00 (d, J=6 Hz, 2H), 3.81 (S, 6H)

EXAMPLE 5

Bis[3,4-Dimethoxybenzaldehyde]trans,trans-Azine 3,4-Dimethoxybenzaldehyde (1 g, 6.018 mmol) was dissolved in methanol (30 ml). Hydrazine hydrate (0.150 g, 0.145 ml, 2.997 mmol, neat liquid) was added via pipette and the reaction solution was stirred overnight at room temperature under nitrogen. The resultant precipitate was isolated by filtration then washed with cold methanol and allowed to dry to yield the title product: $^1$H NMR (300 MHz, DMSO-$d_6$); δ 8.62 (S, 2H), 7.47 (S, 2H), 7.35 (d, J=9 Hz, 2H), 7.05 (d, J=9 Hz, 2H), 3.81 (S, 12H).

EXAMPLE 6

Bis[4-Hydroxybenzaldehyde]trans,trans-Azine

4-Hydroxybenzaldehyde (1 g, 8.19 mmol) was dissolved in methanol (30 ml). Hydrazine hydrate (201 mg, 0.195 ml, 4.01 mmol, neat liquid) was added by syringe and the reaction solution was stirred overnight under nitrogen at room temperature. The resultant precipitate was isolated by filtration and washed in cold methanol to yield yellow flakes (548 mg, 57% yield) of the title product: $^1$H NMR (300 MHz, DMSO-$d_6$); δ 10.04 (S, 2H), 8.53 (S, 2H), 7.67 (d, J=9 Hz, 4H), 7.83 (d, J=9 Hz, 4H).

EXAMPLE 7

Bis[4-Hydroxy-3-Methoxyacetophenone]trans,trans-Azine

4-Hydroxy-3-methoxyacetophenone (1 g, 6.02 mmol) was dissolved in methanol (20 ml). The resultant solution was stirred and hydrazine hydrate (150.68 mg, 3.01 mmol, 0.146 ml, neat liquid) was added by syringe at room temperature. The reaction vessel was stirred at room temperature overnight under nitrogen. The next day (17.5 hours later) the reaction solution was brought to reflux for ten (10) hours. The heat was removed from the reaction solution and it was allowed to stir at room temperature overnight. The next morning the reaction was refluxed for an additional six (6) hours, cooled, and the methanol removed in vacuo to leave a yellow solid. This solid was dissolved in hot ethyl acetate and the solution was filtered and set aside for crystallization. The resultant crystals were isolated by filtration, washed with ethyl acetate and allowed to dry to provide a portion (230 mg) of the title product. An additional crop of crystals (176 mg) formed from the mother liquor upon standing. The two crops of crystals were combined to yield 406 mg, 41% yield of the title product: $^1$H NMR (300 MHz, DMSO-$d_6$); δ 7.64 (S, 2H), 7.33–7.30 (m, 2H) 6.94 (d, J=6 Hz, 2H), 5.81 (S, 2H), 3.97 (S, 6H), 2.28 (S, 6H).

EXAMPLE 8

Bis[3-Ethoxy-4-Hydroxybenzaldehyde]trans,trans-Azine

3-Ethoxy-4-hydroxybenzaldehyde (3 g, 18 mmol) was dissolved in methanol (20 ml). The resultant solution was stirred under nitrogen and hydrazine hydrate (450.5 mg, 9 mmol, 0.44 ml, neat liquid) was added by syringe. The solution turned yellow following the addition of the hydrazine hydrate and a large precipitate began to form. The reaction mixture was stirred overnight at room temperature under nitrogen. The reaction mixture was cooled and the precipitate was isolated by filtration. The precipitate was washed in cold methanol and allowed to dry to provide a pale yellow powder (2.93 g, 99% yield) of the title product: $^1$H NMR (300 MHz, DMSO-$d_6$); δ 9.59 (S, 2H), 8.53 (S, 2H), 7.41 (S, 2H), 7.22 (d, J=6 Hz, 2H), 6.86 (d, J=6 Hz, 2H), 4.05 (g, J=6 Hz, 4H), 1.35 (t, J=6 Hz, 6H).

EXAMPLE 9

Bis[3,5-Dimethoxy-4-Hydroxyacetophenone]trans,trans-Azine 3,5-Dimethoxy-4-hydroxyacetophenone (1 g, 5.1 mmol) was dissolved in methanol (20 ml) with heating. Hydrazine hydrate (127.65 mg, 2.55 mmol, 0.124 ml, neat liquid) was added to the reaction solution and the flask was flushed with nitrogen. Upon addition of hydrazine, a precipitate was formed. The resultant slurry was stirred under nitrogen at room temperature overnight. The next morning the reaction mixture appeared homogeneous. The reaction mixture was then refluxed for 10.5 hours, allowed to cool, and then stirred overnight at room temperature. The following morning, the reaction mixture was again refluxed for three hours. The reaction mixture was then cooled and the solvent was removed in vacuo to yield a brown-yellow solid. The solid was dissolved in hot ethyl acetate and filtered through a short silica plug under vacuum. The filtrate was set aside for crystallization. The resultant solid from the crystallization procedure and was collected by filtration, washed with ethyl acetate and allowed to dry to give 280 mg of a solid. $^1$H NMR (300 MHz, DMSO-$d_6$); δ 8.33 (S, 2H), 86 (S, 4H), 3.74 (S, 12H), 1.97 (S, 6H).

EXAMPLE 10

N-[4-Hydroxy-3-Methoxybenzaldehyde]-N'-[4-Hydroxybenzaldehyde]trans,trans-Azine

N-(3-methoxy-4-hydroxybenzylidene)-N',N'-dimethylhydrazone (500 mg, 258 mmol) was dissolved in 5 ml absolute ethanol. To this solution was added anhydrous hydrazine (413.45 mg, 12.9 mmol, 0.405 ml, neat liquid) and the resulting solution refluxed under nitrogen for 3 hours. After cooling to room temperature, the solution was poured over crushed ice and extracted with ether (2×). The combined organics were washed once with brine, dried over MgSO$_4$, filtered and concentrated to provide as a yellow oil of 4-hydroxy-3-methoxybenzaldehyde hydrazone(crude mixture, assumption of 80% purity, 342.4 mg, 2.06 mmol). The hydrazone was diluted with ethanol (5 ml) and 4-hydroxybenzaldehyde (252 mg, 2.06 mmol) was added to the solution followed bv an ethanol (5 ml) rinse. The resulting solution was stirred at room temperature overnight under nitrogen. The solvent was removed in vacuo to yield a yellow oil. The yellow oil was flash chromatographed on silica (gradient solution of 20% ethyl acetate/hexane to 30% ethyl acetate/hexane) to provide a light yellow solid (200 mg, 29% of the title product) $^1$H NMR (300 MHz, DMSO-$d_6$); δ 9.85 (brS, 2H), 8.5b (d, J=3 Hz, 1H), 8.53 (d, J=3 Hz, 1H), 7.26 (Abq, J–9 Hz, 4H), 7.43 (S, 1H), 7.22 (d, J=9 Hz, 1H), 6.85 (d, J=9 Hz, 1H), 3.81 (S, 3H).

EXAMPLE 11

Bis[3-Methoxybenzaldehyde]trans,trans-Azine

3-Methoxybenzaldehyde (1 g, 7.35 mmol, 0.84 ml) was dissolved in methanol (20 ml). To this solution was added hydrazine hydrate (0.18 g, 3.59 mmol, 0.174 ml, neat liquid) by syringe. The resultant reaction mixture was stirred under nitrogen at room temperature for forty-eight hours. The solution was reduced in vacuo to give a yellow solid. The yellow solid was dissolved in a mixture of ether and hexane and this solution was subjected to a vacuum overnight to yield small yellow crystals. The crystals were redissolved in methanol and recrystallized. The crystals were isolated by filtration to give the title compound: $^1$H NMR (300 MHz, DMSO-$d_6$); δ 8.67 (S, 2H), 7.44–7.38 (m, 6H), 7.10–7.06 (m, 2H) 3.80 (S, 6H).

EXAMPLE 12

Bis[3,4 - Dihydroxybenzaldehyde]trans,trans-Azine 3,4-Dihydroxybenzaldehyde (1 g, 7.24 mmol) was dissolved in methanol (30 ml) to give a dark brown solution.

Hydrazine hydrate (0.177 g, 3.54 mmol, 0.172 ml, neat liquid) was added by syringe to the solution to give a yellow reaction mixture. Precipitate began to form immediately after the addition of the hydrazine. The solution was stirred for forty-eight (48) hours at room temperature under nitrogen. The reaction solution was taken to dryness in vacuo to give a brown solid. The brown solid was triturated with hot ether and ethyl acetate and then filtered. The brown solid was collected and analyzed by N.M.R. which confirmed the presence of title product. $^1$H NMR (300 MHz, DMSO-d$_6$); δ 8.67 (S, 2H) 7.44–7.38 (m, 6H), 7.09–7.06 (m, 2H), 3.80 (S, 6H).

EXAMPLE 13

N-[4-Hydroxy-3-Methoxybenzaldehyde]-N'-[Benzaldehyde]trans,trans-Azine

N-(3-Methoxy-4-hydroxybenzylidene) hydrazone (342.4 mg, 2.06 mmol, crude mixture, 80% purity assumed, prepared as in Example 10) was suspended in ethanol (5 ml). To the suspension was added benzaldehyde (146 mg, 1.376 mmol, 0.1399 ml, neat liquid) dissolved in ethanol (1 ml). The resultant reaction mixture was stirred at room temperature under nitrogen for seventy-two (72) hours. The reaction mixture was chromatographed on silica with a gradient solution (20–30%) of ethyl acetate and hexane. The fraction containing the title product was allowed to crystallize and the resultant crystals were collected by filtration and again recrystallized from hexane to yield purified title product: $^1$H NMR (300 MHz, DMSO-d$_6$); δ 9.67 (S, 1H), 8.68 (S, 1H), 8.58 (S, 1H) 7.85–0 7.83 (m, 2H), 7.50–7.46 (m, 4H), 7.27 (d, J=9 Hz, 1H), 6.87 (d, J=9 Hz, 1H), 3.82 (S, 3H).

EXAMPLE 14

Bis[3,5-(tert-Butyl)-4-Hydroxybenzaldehyde]trans,trans-Azine 3,5-(tert-butyl)4-hydroxybenzaldehyde (1 g, 4.11 mmol) was slurried in methanol (30 ml). To this slurry was added hydrazine hydrate (0.101 g, 2.01 mmol, 0.097 ml, neat liquid) by syringe to give a light purple reaction solution. The reaction solution was stirred overnight at room temperature under nitrogen to yield a deep yellow precipitate. The precipitate was collected by filtration, washed with cold methanol and ether, and allowed to dry to give the title product: $^1$H NMR (300 MHz, DMSO-d$_6$); δ 8.60 (S, 2H), 7.63 (S, 4H), 7.45 (S, 2H) 1.39 (S, 36H).

EXAMPLE 15

Bis[Pyridine-4-Carboxaldehyde]trans,trans-Azine

Under a nitrogen atmosphere, pyridine-4-carboxaldehyde (1 g, 9.34 mmol, 0.89 ml, neat liquid) was dissolved in methanol (20 ml). To the solution was added hydrazine hydrate (0.228 g, 4.56 mmol, 0.221 ml, neat liouid) by syringe. The resultant reaction solution was stirred overnight at room temperature under a nitrogen atmosphere. The resultant bright yellow precipitate was isolated by filtration and washed with cold methanol and ether to yield the title product: $^1$H NMR (300 MHz, DMSO-d$_6$); δ 8.74–8.67 (m, 6H), 7.79 (d, J=6 Hz, 4H)

EXAMPLE 16

N-(3,5-di(tert-Butyl)-4-Hydroxybenzylidene)-p-Methoxyaniline 3,5-di(Tert-butyl)-4-hydroxybenzaldehyde (1 g, 4.11 mmol) was dissolved in methanol (30 ml). To this solution was added p-anisidine (0.51 g, 4.11 mmol). The resultant reaction solution was stirred at room temperature under nitrogen for two (2) hours and the solution was taken to dryness in vacuo. The resultant oil was azeotroped with methanol (2×), ether (1×), a mixture of ethyl acetate/hexane (1×), and methanol (1×). The oil was left in vacuo overnight which began crystallization of the oil. The crystals were then dissolved in a mixture of ether and hexane. Dark flakes of p-anisidine were filtered out of the solution, the mother liquor was reduced with low heat, resulting in crystals of the title product which were collected by filtration: $^1$H NMR (300 MHz, CDCl$_3$); δ 8.38 (S, 1H), 7.72 (S, 2H), 7.19 (d, J=9 Hz, 1H), 6.90 (d, J=9 Hz, 2H), 5.58 (S, 1H), 3.83 (S, 3H).

EXAMPLE 17

N-(3-Methoxy-4-Hydroxybenzylidene)-p-Methoxyaniline

3-Methoxy-4-hydroxybenzaldehyde (vanillin, 1 g, 6.57 mmol) was dissolved in methanol (30 ml). To this solution was added p-anisidine (0.810 g, 6.57 mmol) and the resultant reaction solution was stirred overnight under nitrogen at room temperature. The reaction solution was taken to dryness in vacuo with the application of heat. The resultant solid was azeotropically mixed with methanol (2×), ether (1×), and again with methanol (2×) to yield yellow crystals. The crystals were triturated with hot ether to yield the title product: $^1$H NMR (300 MHz, CDCl$_3$); δ 8.36 (S, 1H) 7.60 (S, 1H), 7.30–7.17 (m, 3H), 7.05–6,91 (m, 3H), 6.10 (S, 1H), 3.97 (S, 3H), 3.83 (S, 3H)

EXAMPLE 18

N-(3,5-Dimethoxy-4-Hydroxybenzylidene)-p-Methoxyaniline 3,5-Dimethoxy-4-hydroxybenzaldehyde (1 g, 5.46 mmol) was added to methanol (30 ml). To this solution was added p-anisidine (672 mg, 5.46 mmol) and the resultant reaction solution was stirred for forty-eight hours at room temperature under nitrogen. The reaction solution began to rapidly produce precipitate. At the end of this time, the reaction solution was placed in the freezer and the resultant precipitate was isolated by filtration. The precipitate was washed with methanol and then ether to give a light yellow solid that was the title product: $^1$H NMR (300 MHz, CDCl$_3$); δ 8.35 (S, 1H) 7.26–7.16 (m, 4H), 6.93 (d, J=9 Hz, 2H), 5.81 (S, 1H) 3.98 (S, 6H), 3.84 (S, 3H).

EXAMPLE 19

N-(3,5-Dimethoxy-4-Hydroxybenzylidene)-p-Fluoroaniline 3,5-Dimethoxy-4-hydroxybenzaldehyde (1 g, 5.46 mmol) was dissolved in methanol (30 ml) and to this solution was added 4-fluoroaniline (600 mg, 5.46 mmol, 0.51 ml). The resultant reaction solution was stirred for forty-eight (48) hours at room temperature under nitrogen. The reaction solution was then cooled in the freezer and the resultant precipitate was isolated by filtration and washed with cold methanol and ether. The isolated light yellow powder was the title product: $^1$H NMR (300 MHz, CDCl$_3$); δ 8.31 (S, 1H), 7.20–7.04 (m, 4H) 5.85 (S, 1H), 3.98 (S, 6H).

EXAMPLE 20

N-(3,5-Dimethoxy-4-Hydroxybenzylidene)-p-Bromoaniline 3,5-Dimethoxy-4-hydroxybenzaldehyde (1 g, 5.46 mmol) was dissolved in methanol (50 ml) and 4-bromoaniline (939 mg, 5.46 mmol) was added. The resultant reaction solution was stirred overnight at room temperature under nitrogen to give a precipitate that was collected by filtration to yield light yellow fine crystals (860 mg) of the title product: $^1$H NMR (300 MHz, CDCl$_3$); δ 8.30 (S, 1H), 7.49 (d, J=9 Hz, 2H), 7.16 (S, 2H), 7.07 (d, J=9 Hz, 2H), 5.86 (S, 1H), 3.98 (S, 6H).

EXAMPLE 21

R-N'-(3,5-Dimethoxy-4-Hydroxybenzylidene)-5-Amino-1,3,4-Thiadiazole 3,5-Dimethoxy-4-hydroxybenzaldehyde (500 mg, 2.73 mmol) and 5-amino-1,3,4-thiadiazole (276 mg, 2.73 mmol) were combined under nitrogen. The compounds were heated to 120° C. with an oil bath and were stirred for forty minutes at that temperature. The reaction solution was allowed to cool and the resultant opaque yellow solid was dissolved in methanol. The methanol solution was taken to dryness in vacuo and the resultant solid was dissolved in a mixture of ethyl acetate and ether. The ethyl acetate-ether mixture yielded yellow crystals (260 mg) of crude product. The crude product was chromatographed on silica gel by flash chromatography with 2% methanol/methylene chloride. The product-containing fraction was taken to dryness in vacuo and the resultant orange solid was triturated with hot ethyl acetate to give the title product: $^1$H NMR (300 MHz, DMSO-d$_6$); δ 9.38 (S, 1H), 8.84 (S, 1H), 7.36 (S, 2H), 3.84 (S, 6H).

EXAMPLE 22

5-N'-(3-Methoxy-4-Hydroxybenzylidene)-5-Amino-1,3,4-Thiadiazole

Vanillin (500 mg, 3.3 mmol) and 5-amino-1,3,4-thiadiazol (333 mg, 3.3 mmol) were combined under nitrogen. The components were heated at 110° C. for twenty minutes. The reaction mixture was allowed to cool and the resultant solid was dissolved in a mixture of methanol and ethyl acetate. The solution was taken to dryness in vacuo to yield a yellow solid. The yellow solid was dissolved in hot ethyl acetate and allowed to sit overnight. The resultant yellow solid (260 mg) was recrystalized in ethyl acetate and the crystals were collected by filtration. The crystals were determined to be thiadiazole starting material. The mother liquor from the above crystallization attempt was taken to dryness and flash chromatographed in 100% ethyl acetate over a silica column to yield a yellow flakes of the title product: $^1$H NMR (300 MHz, DMSO-d$_6$); δ 9.37 (S, 1H), 8.84 (S, 1H), 7.59 (S, 1H), 7.50 (d, J=6 Hz, 1H), 6.93 (d, J=6 Hz, 1H), 3.85 (S, 3H).

EXAMPLE 23

N-(3,5-Dimethoxy-4-Hydroxybenzylidene)Aniline 3,5-Dimethoxy-4-hydroxybenzaldehyde (1 g, 5.46 mmol) was dissolved in methanol (50 ml) and aniline (560 mg, 6.01 mmol, 0.35 ml, neat liquid) was added to the solution by syringe. The resultant reaction mixture was stirred overnight at room temperature under nitrogen then taken to dryness in-vacuo. The yellow crystals thus obtained were triturated with hot ether, allowed to cool, filtered and the collected solid was washed with ether to yield the title product: $^1$H NMR (300 MHZ, CDCl$_3$) δ , 8.33 (S, 1H), 7.42–7.39 (m, 2H), 7.21–7.18 (m, 5H), 5.84 (S, 1H), 3.98 (S, 6H)

We claim:

1. A method for inhibiting the effects of the oxidative burst of phagocyte leukocytes which comprises administering to a host a pharmaceutical composition comprising an effective amount of compound of the formula:

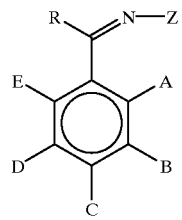

a) A, B, C, D, E independently can be hydroxy, thiol, $C_1$ to $C_6$ alkyl, $C_1$ to $C_4$ alkoxy, halo, a hydrogen atom, $C_1$ to $C_4$ alkylthio, amino, or mono- or di-substituted amino;
b) R is $C_1$ to $C_6$ alkyl, $C_7$ to $C_{12}$ alkylphenyl, $C_7$ to $C_{12}$ substituted alkylphenyl, or a hydrogen atom;
c) Z is heterocyclic ring, phenyl, or substituted phenyl; or
(d) a group of the formula:

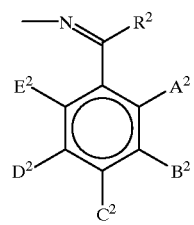

Wherein $A^2$, $B^2$, $C^2$, $D^2$, $E^2$ or $R^2$ can be the same or different as A, B, C, D, E or R, respectively, and are as defined as A, B, C, D, E, and R, respectively.

2. A method of claim 1, wherein Z is a group of the formula:

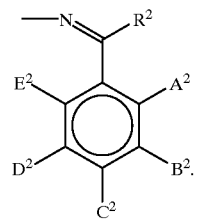

3. A method of claim 2, wherein R and $R^2$ are chosen from the group consisting of a hydrogen atom and methyl; and A, B, C, D, E, $A^2$, $B^2$, $C^2$, $D^2$, $E^2$ are chosen from the group consisting of a hydrogen atom, hydroxy, methoxy, t-butyl, bromo, or ethoxy.

4. A method of claim 3, wherein $R^2$ and $A^2$, $B^2$, $C^2$, $D^2$, $E^2$ are the same as R, A, B, C, D, and E, respectively.

5. A method of claim 4, wherein R and $R^2$ are methyl.

6. A method of claim 5, wherein C and $C^2$ are hydroxy; B and $B^2$ are methoxy; and A, D, E, $A^2$, $D^2$, and $E^2$ are a hydrogen atom.

7. A method of claim 4, wherein R and $R^2$ are a hydrogen atom.

8. A method of claim 7, wherein C and $C^2$ are hydroxy, and A, $A^2$, E, and $E^2$ are a hydrogen atom.

9. A method of claim 8, wherein B and $B^2$ are methoxy, and D and $D^2$ are a hydrogen atom.

10. A method of claim 8, wherein B and $B^2$ are methoxy, and D and $D^2$ are bromo.

11. A method of claim 8, wherein B, $B^2$, D, and $D^2$ are a hydrogen atom.

12. A method of claim 3, wherein at least one of $R^2$, $A^2$, $B^2$, $C^2$, $D^2$, and $E^2$ is different from the corresponding R, A, B, C, D, and E.

13. A method of claim 12, wherein R and $R^2$ are a hydrogen atom.

14. A method of claim 13, wherein C and $C^2$ are chosen from the group consisting of a hydrogen atom and hydroxy; B and $B^2$ are chosen from the group consisting of a hydrogen atom and methoxy; and A, $A^2$, D, $D^2$, E, and $E^2$ are a hydrogen atom.

15. A method of claim 14, wherein C and $C^2$ are a hydroxy group, B is a hydrogen atom, and $B^2$ is a methoxy group.

16. A method of claim 14, wherein B is methoxy, C is hydroxy, and $C^2$ is a hydrogen atom.

17. A method of claim 12, wherein R and $R^2$ are methyl.

18. A method of claim 1, wherein Z is a heterocyclic ring, phenyl, or a substituted phenyl.

19. A method of claim 18, wherein A, B, C, D, and E are chosen from the group consisting of a hydrogen atom, hydroxy, methoxy, and tert-butyl; and R is a hydrogen atom or methyl.

20. A method of claim 19, wherein R is a hydrogen atom.

21. A method of claim 20, wherein Z is phenyl or substituted phenyl.

22. A method of claim 21, wherein the substituents are methoxy or bromo.

23. A method of claim 22, wherein C is hydroxy.

24. A method of claim 23, wherein B and D are methoxy, A and E are a hydrogen atom, and Z is para-methoxyphenyl.

25. A method of claim 23, wherein B is methoxy, A, D, and E are a hydrogen atom, and Z is para-methoxyphenyl.

26. A method of claim 23, wherein B and D are methoxy, A and E are a hydrogen atom, and Z is para-bromophenyl.

27. A method of claim 23, wherein B and D are methoxy, A and E are a hydrogen atom, and Z is phenyl.

28. A method of treating free-radical-generating inflammatory conditions in a mammal, comprising administering an effective amount of a pharmaceutical composition comprising a compound of the formula:

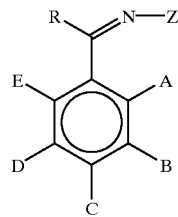

a) A, B, C, D, E independently can be hydroxy, thiol, $C_1$ to $C_6$ alkyl, $C_1$ to $C_4$ alkoxy, halo, a hydrogen atom, $C_1$ to $C_4$ alkylthio, amino, or mono- or di-substituted amino;
b) R is $C_1$ to $C_6$ alkyl, $C_7$ to $C_{12}$ alkylphenyl, $C_7$ to $C_{12}$ substituted alkylphenyl, or a hydrogen atom;
c) Z is heterocyclic ring, phenyl, or substituted phenyl; or
(d) a group of the formula:

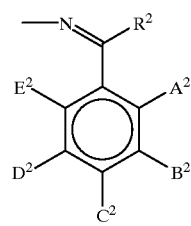

Wherein $A^2$, $B^2$, $C^2$, $D^2$, $E^2$ or $R^2$ can be the same or different as A, B, C, D, E or R, respectively, and are as defined as A, B, C, D, E, and R, respectively; and a pharmaceutically-acceptable carrier.

29. A method of claim 28, wherein said condition is selected from the group consisting of inflammatory bowel disease, rheumatoid arthritis, granulomatous disease, reperfusion injury from heart attack or stroke, and asthma.

30. The method of claim 29, wherein said condition is rheumatoid arthritis.

31. The method of claim 29, wherein said condition is reperfusion injury From heart attack or stroke.

32. The method of claim 29, wherein said condition is inflammatory bowel disease.

33. The method of claim 29, wherein said condition is asthma.

* * * * *